(12) United States Patent
McClure et al.

(10) Patent No.: US 6,386,706 B1
(45) Date of Patent: May 14, 2002

(54) VISUAL FUNCTION TESTING WITH VIRTUAL RETINAL DISPLAY

(75) Inventors: Richard J. McClure, San Diego; R. Kemp Massengill, Leucadia; Dariusz Wroblewski, San Diego, all of CA (US); Johannes Braeuning, Ostfildern (DE)

(73) Assignee: Virtual-Eye.COM, Leucadia, CA (US)

( * ) Notice: Subject to any disclaimer, the term of this patent is extended or adjusted under 35 U.S.C. 154(b) by 0 days.

(21) Appl. No.: 09/467,360

(22) Filed: Dec. 20, 1999

Related U.S. Application Data

(63) Continuation-in-part of application No. 09/179,112, filed on Oct. 26, 1998, now Pat. No. 6,027,217, which is a continuation-in-part of application No. 08/864,331, filed on May 28, 1997, now Pat. No. 5,898,474, which is a continuation-in-part of application No. 08/700,754, filed on Jul. 31, 1996, now Pat. No. 5,864,384.

(60) Provisional application No. 60/136,151, filed on May 27, 1999, provisional application No. 60/165,082, filed on Nov. 12, 1999, provisional application No. 60/067,521, filed on Dec. 4, 1997, and provisional application No. 60/089,817, filed on Jun. 19, 1998.

(51) Int. Cl.⁷ .............................................. A61B 3/02
(52) U.S. Cl. ..................................................... 351/237
(58) Field of Search ................................. 351/205, 208, 351/209, 210, 221, 222, 223, 224, 226, 239, 246, 237, 243; 345/7, 8

(56) References Cited

U.S. PATENT DOCUMENTS

| | | |
|---|---|---|
| 5,461,436 A | 10/1995 | Campbell .................... 351/242 |
| 5,467,104 A | 11/1995 | Furness, III et al. ............ 345/8 |
| 5,589,897 A | 12/1996 | Sinclair et al. |
| 5,596,339 A | 1/1997 | Furness, III et al. ............ 345/8 |
| 5,659,327 A | 8/1997 | Furness, III et al. ............ 345/8 |
| 5,701,132 A | 12/1997 | Kollin et al. ................... 345/8 |

(List continued on next page.)

FOREIGN PATENT DOCUMENTS

DE          195 40 802.0          11/1993          ............ A61B/3/00

OTHER PUBLICATIONS

Adams, A.; Clinical Measures of Central Vision Function in Glaucoma and Ocular Hypertension; Jun., 1987; Arch Ophthalmol, vol. 105; pp. 782–787.

Adams, A.; Spectral Sensitivity and Color Discrimination Changes in Glaucoma and Glaucoma–suspect Patients; Oct., 1982; Invest. Ophthalmol. Vis. Sci.; vol. 23, No. 4; pp. 516–524.

Airaksinen, P.; Color Vision and Retinal Nerve Fiber Layer in Early Glaucoma; Feb., 1986; American Journal of Ophthalmalogy vol. 101; pp. 208–213.

Applegate, R.; Entoptic Evaluation of Diabetic Retinopathy; Apr., 1997; Investigative Ophthalmology & Visual Science, vol. 38, No. 5; pp. 783–791.

(List continued on next page.)

*Primary Examiner*—George Manuel
(74) *Attorney, Agent, or Firm*—Gerald W. Spinks (57) ABSTRACT

A system for testing and quantifying visual field and other visual function information in a head-mounted virtual reality environment, utilizing a directed image formation device for scanning of an image onto the retina of the test subject. A method and an apparatus are also provided for utilizing a central neural network and a central data bank to perform automatic interpretation of the visual function test parameters obtained in a plurality of visual field testing systems, for a plurality of patients, with control and response signals being transmitted via the Internet. The data produced by the testing systems are automatically analyzed and compared with patterns on which the neural network was previously trained, and clinical diagnoses for pathological conditions are thereby suggested to the respective clinician for each patient.

31 Claims, 5 Drawing Sheets

U.S. PATENT DOCUMENTS

| | | | |
|---|---|---|---|
| 5,751,465 A | 5/1998 | Melville et al. | 359/213 |
| 5,894,339 A | 4/1999 | Hosoi | |
| 5,903,397 A | 5/1999 | Melville et al. | 359/630 |
| 5,969,871 A | 10/1999 | Tidwell et al. | 359/620 |
| 6,045,227 A * | 4/2000 | Stewart et al. | 351/237 |
| 6,139,152 A * | 10/2000 | Ghahramani | 351/243 |
| 6,290,357 B1 * | 9/2001 | Massengill et al. | 351/209 |

OTHER PUBLICATIONS

Applegate, R.; Entoptic Visualization of the Retinal Vasculature Near Fixation; Oct., 1990; Investigative Ophthalmology, vol. 31, No. 10; pp. 2088–2098.

Bartley, S.; Vision A Study of its Basis; 1963; pp. 57–71.

Bethke, W.; The Power of Second Sight; Jan., 1997; Review of Ophthalmology; p. 21.

Bottari, J.; Blue Field Entoptic Study: Diurnal and Long Term Fluctuation of Leukocyte Characteristics; www.c-s.tufts.ecu/~vanvo/ARVO96B.html; 1 p.

Breton, M.; Age Covariance Between 100–Hue Color Scores and Quantitative Perimetry in Primary Open Angle Glaucoma; May, 1987; Arch Ophthalmol, vol. 105; pp642–645.

Burstein, R.; Virtual Retinal Display; 1997; HITLab Review, No. 10; 2 pages.

Business Communications Co.; Display Detects Retinal Diseases; Jun., 1999; Microtechnology NewsVvol. 5, No. 7; 2 pages.

Caprioli, J.; Early Diagnosis of functional Damage in Patients With Glaucoma; Jan., 1997; Arch Ophythalmol vol. 115; pp. 113–114.

CMP Media Inc.; Two Eye Virtual Retinal Display Tech; Jun., 1997; EE Times Issue 957; 1 page.

Davies, E.; Macular Blood Flow Response to Acute Reduction of Plasma Glucoses in Diabetic Patients Measured by the Blue Light Entoptic Technique; Mar., 1989; Ophthalmalogy vol. 97 No. 2; pp. 160–164.

Donnelly, J.; Here's Light in Your Eye, Kid; Mar., 1999; Military Training Technology, vol. 4, Issue 1; 3 pages.

Drance, S.; Acquired Color Vision Changes in Glaucoma; Jul. 1980/Arch Ophthalmol vol. 99; pp. 829–831.

Falcao–Reis, F.M.; Mar., 1991; Macular Colour Sensitivity in Ocular Hypertension and Glaucoma; British Journal of Ophthalmology; 1991, 75; pp. 598–602.

Fellius, J.; Functional Characteristics of Blue–on–Yellow Perimetric Thresholds in Glaucoma; Feb. 8, 1995; Investigative Ophthalmology & Visual Science, vol. 36, No. 8; pp. 1665–1674.

Flammer, J.; Correlation Between Color Vision Scores and Quantitative Perimetry in Suspected Glaucoma; Jan., 1983; Arch Ophthalmol, vol. 102; pp. 38–39.

Geddes, J.; New Personal Display Technology; May, 1999; Image Society Feature Articles; www.public.asu.edu/~image/NEWS/NewsFeatureA.html; 2 pages.

Gunduz, K.; Color Vision Defects in Ocular Hypertension and Glaucoma; Jan., 1988; Arch Ophthalmol vol. 106; pp. 929–935.

Hamill, T.; Correlation of Color Vision Deficits and Observable Changes in the Optic Disc in a Population of Ocular Hypertensives; Jun., 1984; Arch Ophthalmol vol. 102; pp. 1637–1639.

Hart, W.; Color Contrast Perimetry; Nov., 1984; Ophthalmology vol. 92, No. 6; pp. 768–776.

Hart, W.; Color Perimetry of Glaucomatous Visual Field Defects; Oct., 1983; Ophthalmalogy vol. 91, No. 4; pp. 338–346.

Hart, W.; Color Contrast Perimetry; Jan. 1983; Investigative Ophthalmology & Visual Science vol. 25; pp400–413.

Hart, W.; Glaucomatous Visual Field Damage; Feb. 1989; Investigative Ophthalmology & Visual Science, vol. 31, No. 2, pp. 359–367.

Heron, G., Central Visual Fields For Short Wavelength Sensitive Pathways in Glaucoma and Ocular Hypertension; Jul. 1987; Investigative Ophthalmology & Visual Science vol. 29 No. 1; pp 64–72.

Humphrey Instruments; Humphrey Blue–Yellow Perimetry; advertisement; date unknown; 1 page.

Humphrey Instruments; Humphrey Field Analyzer II; date unknown; www.humphrey.com; 1 page.

Interzeag AG; Blue/Yellow Perimetry; Jun., 1997; Ocular Surgery News; 1 page.

Interzeag AG; Clairvoyant Octopus; Jul. 1997; Ocular Surgery News; 2 pages.

Johnson, C.; Blue–on–Yellow Perimetry Can Predict the Development of Glaucomatous Visual Field Loss; Jan. 1993; Arch Ophthalmol vol. 111; pp. 645–650.

Johnson, C.; Progression of Early Glaucomatous Visual Field Loss as Detected by Blue–on–Yellow and Standard White–on–WhiteAutomated Perimetry;Jan. 1993; Arch Ophthalmol vol. 111; pp. 651–656.

Johnson, C.; Short–Wavelength Automated Perimetry in Low–,Medium–. and Hight–risk Ocular Hypertensive Eyes; Jan. 1995;Arch Ophthalmol vol. 113; pp. 70–76.

Kollin, J.; Optical Engineering Challenges of the Virtual Retinal Display; 1995; Published by Society of Photo–Optical Instrumentation Engineers; 12 pages.

Lewis R.; Automated Perimetry and Short Wavelength Sensitivity in Patients with Asymmetric Intraocular Pressures; Nov. 1992; Graefe's Archive for Clinical and Experimental Ophthalmology; pp. 274–278.

Logan, N.; Detecting Early Glaucomatous Visual Field Changes With A blue Stimulus; Jan. 1983; American Journal of Ophthalmology vol. 95; pp. 432–434.

Massengill, R., GlobalMed VF–2400 Telemedicine/Autointerpretation System for Visual Function Testing; Nov. 1998; Press release for the American Academy of Ophthalmology Meeting; 7 pages.

Microvision; Web Site and Related Press Releases; Nov. 1999; www.mvis.com; Entire volume.

Microvision; Microvision Announces Breakthrough with Super–Bright Light–Emitting Diodes; Nov. 1999; www.mvis.com; 2 pages.

Microvision; Microvision and Boeing Collaborate to Develop Cockpit of the Future; Mar. 1999; www.mvis.com; 2 pages.

Microvision; Microvision Delivers Groundbreaking Helmet–Mounted Display; Mar. 1999; www.mvis.com; 2 pages.

Microvision; Virtual Retinal Display; May 1999; www.mvis.com; 9 pages.

Microvision; Microvision Chosen by Wallace–Kettering Neuroscience Institute; Au. 1998; www.mvis.com; 4 pages.

Mindel, J.; Visual Field Testing With Red Targets; Jul. 1982; Arch Ophthalmol vol. 101; pp. 927–929.

Moss, I.; The Influence of Age–Related Cataract on Blue–onYellow Perimetry; Nov. 1994; Investigative Ophthalmology & Visual Science vol. 36, No. 5; pp. 764–773.

Moses, R.; Entoptic and Allied Phenomena; 1981; Adler's Physiology of the Eye; pp. 562–574.

Motolko, M.; The Early Psychophysical Disturbances in Chronic Open–angle Glaucoma; Nov. 1981; Arch Ophthalmol vol. 100; pp. 1632–1634.

Ocular Surgery News; Beta Sites; Apr. 1999; 1 page.

Plummer, D.; The Utility of Entoptic Perimetry as a Screening Test for Cytomegalovirus Retinitis; Feb. 1999; Arch Ophthalmol vol. 117; pp. 202–207.

Quigley, H.; Chronic Glaucoma Selectively Damages Large Optic Nerve Fibers; Oct. 1986; Investigative Oophthalmology & Visual Science vol. 28 No. 6; pp. 913–920.

Sample, P.; Color Perimetry for Assessment of Primary Open–Angle Glaucoma; Sep. 1990; Investigative Ophthalmology & Visual Science vol. 31 No. 9; pp. 1869–1875.

Sample, P.; Isolating the Color Vision Loss in Primary Open–angle Glaucoma; Sep. 1988; American Journal of Ophthalmology vol. 106 No. 6; pp. 686–691.

Sample, P.; Progressive Color Visual Field Loss in Glaucoma; Dec. 1991; Investigative Ophthalmology & Visual Science vol. 33 No. 6; pp. 2068–2071.

Sample, P.; Short–wavelength Automated Perimetry Without Lens Density Testing; May 1994; American Journal of Ophthalmology vol. 118 No. 5; pp. 632–641.

Sample, P.; Short–wavelength Color Visual Fields in Glaucoma Suspects at Risk; Oct. 1992; American Journal of Ophthalmology vol. 115 No. 2; pp. 225–233.

Stoll, D.; Retinal Scanning Leads HMD Race; Dec. 1998; Photonics Online; 7 pages.

Wild, J.; The Statistical Interpretation of Blue–on–Yellow Visual Field Loss; Jul. 1994; Investigative Ophthalmology & Visual Science vol. 36 No. 7; pp. 1398–1410.

Yamazaki, Y.; A Comparison of the Blue Color Mechanism in High–and Low–tension Glaucoma; Jun. 1988; Ophthalmology vol. 96 No. 1; pp. 12–15.

Yamazaki, Y.; Correlation Between Color Vision and Highest Intraocular Pressure in Glaucoma Patients; Jul. 1988; American Journal of Ophthalmology Vo. 106 No. 4; pp 397–399.

Yu, T.; Peripheral Color Contrast; Apr. 1991; Investigative Ophthalmology & Visual Science vol. 32 No. 10; pp. 2779–2789.

* cited by examiner

VISUAL FUNCTION TESTING WITH VIRTUAL RETINAL DISPLAY

CROSS REFERENCE TO RELATED APPLICATIONS

This is a continuation-in-part patent application of U.S. patent application Ser. No. 09/179,112, filed on Oct. 26, 1998, now U.S. Pat. No. 6,027,217 and entitled "Automated Visual Function Testing Via Telemedicine," which is a conitinuation-in-part of prior application Ser. No. 08/700, 754, filed Jul. 31, 1996, entitled "Visual Field Testing Method and Apparatus Using Virtual Reality", now U.S. Pat. No. 5,864,384; and prior application Ser. No. 08/864,331, filed May 28, 1997, entitled "Visual Field Testing Method and Apparatus", now U.S. Pat. No. 5,898,474. This application also claims priority from U.S. Provisional Patent Application Ser. No. 60/136,151, filed on May 27, 1999, and U.S. Provisional Patent Application Ser. No. 60/165,082, filed on Nov. 12, 1999, both entitled "Visual Field Testing with Virtual Retinal Display." The parent application also claimed priority from Provisional U.S. Patent Application No. 60/067,521, filed Dec. 4, 1997, entitled "Automated Visual Function Testing in Virtual Reality", and Provisional U.S. Patent Application No. 60/089,817, filed Jun. 19, 1998, entitled "Telemedicine for Autointerpretation of Visual Field Testing."

STATEMENT REGARDING FEDERALLY SPONSORED RESEARCH OR DEVELOPMENT

Not Applicable

BACKGROUND OF THE INVENTION

1. Field of the Invention

This invention is in the field of optical testing of the sensitivity of the eye to light, in particular, visual field evaluation.

2. Background Information

On a world-wide basis, glaucoma is one of the leading causes of blindness. Unlike cataract blindness, which is correctable with modern surgical techniques, blindness from glaucoma is permanent. The target organ of glaucoma is the optic nerve, which transmit signals of light from the retina to the brain. No known method is available for repairing, or transplanting, an injured optic nerve.

A major diagnostic problem is that visual loss from glaucoma is almost without exception painless. The patient is not aware of the ravages of glaucoma until it is too late. To compound the problem, the intraocular pressure in glaucoma is often not elevated (termed "low-tension" glaucoma), and therefore reliance upon tonometry to measure the patient's intraocular pressure frequently leads to a blatantly false sense of security. The patient is told that glaucoma is not present, when, in reality, the disease is insidiously attacking the patient's optic nerve, causing irreversible neurological damage to the visual system.

Visual field testing is mandatory for glaucoma diagnosis and treatment. The current gold standard of measurement of optic nerve function is visual field testing, called "perimetry." A problem with this technology, however, is that far too many of the examiners performing visual field testing are inadequately trained to recognize subtle patterns in the patient's visual field indicative of glaucoma (or other neurological disease). Such misdiagnosis, which is unfortunately frequent, again gives the patient a false sense of security.

Millions upon millions of patients throughout the world have glaucoma and are completely unaware of this. The particularly sad aspect of glaucoma blindness is that it is generally preventable with proper diagnosis and treatment. The proposed invention, which incorporates the use of telemedicine for real-time feedback and for autointerpretation of visual field performance, along with a Virtual Retinal Display, will play a major role in eliminating the all-too-common errors in visual field interpretation and the unnecessary blindness which accompanies such ignorance. By making the proper diagnosis virtually instantaneously over the Internet or other telemetric vehicle, glaucoma treatment can be instituted. Millions of patients will be spared the ravages of glaucoma.

In addition to testing for glaucomatous damage to the optic nerve, visual field testing is also used to test for a variety of neurological disorders, including cerebrovascular accidents ("strokes"), trauma, brain tumors, and other diseases. The proposed invention, which incorporates real-time feedback to monitor the patient's performance, and accurate, instantaneous diagnosis available through autointerpretation on a world-wide telemetric basis, addresses a major medical need.

With the huge data base developed by a large-scale, world-wide telemedicine system, leading international experts on glaucoma and other neurological diseases can be employed to improve the accuracy of the entire system.

Investigational work has been done on the use of neural nets "trained to interpret the visual fields from an automated perimeter," as described in "Interpretation of Automated Perimetry for Glaucoma by Neural Net," by Goldbaum, et al. Spenceley, et al. have also published work in the field in an article entitled, "Visual Field Analysis Using Artificial Neural Networks." Brigatti, Hoffman, and Caprioli have worked with neural networks for glaucoma identification, as described in their article entitled, "Neural Networks to Identify Glaucoma With Structural and Functional Measurements." These works are limited to conventional globe-like perimeter systems.

Visual field testing is mandatory for glaucoma diagnosis and treatment, as well as for confirmatory diagnosis of many neurological disorders affecting the optic pathways and the brain. Conventional visual field testing is performed utilizing a cupola-like globe, into which the patient fixates gaze during the testing process, attempting to respond to light stimuli which appear momentarily in the field of view. Major obstacles to patient friendliness are found with conventional visual field testers, and patients consider these methods of visual field analysis troublesome. More common are expressions of frustration, helplessness, boredom, claustrophobia, and, occasionally, anger.

In U.S. Pat. No. 5,864,384 and U.S. Pat. No. 5,898,474, visual fields are performed utilizing a virtual reality testing system employing goggles or other appropriate head gear to circumvent the problems associated with forcing patients to stare into a conventional globe visual field tester. These head-mounted display systems afford the patient freedom of head and body movement, thus eliminating the claustrophobia, tedium, and anxiety often associated with gazing into a stationary conventional globe. A computerized eye movement control system, which moves the stimulus presentation in response to eye movement, enhances patient freedom.

However, all currently known systems for visual field testing involve displaying an image on a physical screen of some sort, which is then viewed by the user. Drawbacks include insufficient brightness in daylight, and limited image resolution and yield.

BRIEF SUMMARY OF THE INVENTION

A head-mounted Virtual Retinal Display (VRD) system is utilized to present to a patient computer-controlled and sequenced test stimuli, thus measuring the patient's field of view (the "visual field") and abnormalities thereof. The virtual retinal display projects a sequentially scanned train of light pulses in such a way as to "paint" an image onto the retina, much as a television raster method generates a television picture. The brain integrates the sequential signals received by the retina, to perceive the "picture" as a whole, which may be updated as frequently as desired by the associated computer, to carry on the visual field test, or tests of other visual functions. A gaze sensor, which may be multi-element, is incorporated so as to allow the gaze to be detected in a small solid angular range and, within this range, the effective fixation is deemed to be maintained. The software in the associated computer provides the generation, via the virtual retinal display, of an interest-fixation icon which encourages the gaze to trace its motion within the allowed solid angle, thus avoiding fixation fatigue. The software keeps track of the location of the test point frame of reference within that solid angle of displacement, so as to provide accurate mapping of test data on the field of view presented to the retina.

A significant advantage of the present system is that it provides relief from the stress of being required to concentrate one's gaze at a fixed location, without head movement. Freedom of movement of the head and body in this system reduces the stress and tedium of visual function testing, thereby enhancing test performance. The present invention can be used for performing quantitative visual field, and other visual function testing, on patients of ophthalmologists, optometrists, neurologists, and other medical practitioners.

Importantly, this new testing system achieves greatly increased brightness in daylight, and greatly enhanced image resolution. Also, since the head-gear can exclude light, ambient light may not be of concern, allowing visual function testing in any room, even allowing the testing of several subjects in the same room. The present invention can be employed with a neural network, or other autointerpretation system. Further, the present invention can also be employed with global network linkage via the Internet, or other suitable transmission method, for purposes of interpretation.

In addition to visual field testing, it is within the scope of this invention to provide other virtual reality, computer-driven, interactive testing capability, such as for visual acuity and color testing. The presently-described invention uses a data processing system to provide automatic interpretation of visual field and other test data received from testing apparatus in a system which can feature a virtual retinal display system. Using virtual reality and associated head-gear configuration in an interactive computerized system allows unprecedented freedom of movement of the head and body, thus minimizing or even eliminating the stress and fatigue common with conventional non-virtual reality visual field testing systems.

The combination of automatic visual field interpretation with a head-mounted virtual retinal display system is unique and novel. The use of telemedicine for centralized interpretation of visual field testing at remote locations, and interactively modulating the performance of the patient is likewise unique and novel.

Audio feedback stimuli, such as voice, or a tone or series of tones, or tactile feedback stimuli, such as a vibration, monitor the test performance in real-time. These stimuli are generated and controlled by software in an associated computer, which receives interactive feedback stimuli from the patient. The content of the software is dictated by the need to provide technically acceptable protocols, such as for examining wide and narrow fields of view, selected areas, such as the blind spot or the fovea, and measurements of thresholds for sensitivity to light intensity, or, if desired, color. Active feedback sensing alerts the system to patient loss of attention in general, or loss of fixation in particular, for notation and reiteration of test stimuli. The system is configured to allow test stimuli to be presented to one eye at a time, or to both eyes simultaneously. Individual test points are reiterated when a result is found to be inconsistent with a predetermined norm.

The novel features of this invention, as well as the invention itself, will be best understood from the attached drawings, taken along with the following description, in which similar reference characters refer to similar parts, and in which:

DETAILED DESCRIPTION OF THE INVENTION

The present invention for performing visual function testing incorporates a technology called virtual retinal display, as disclosed in U.S. Pat. No. 5,467,104, and in U.S. Pat. No. 5,596,339, which are incorporated herein by reference. Virtual retinal display technology utilizes a photon generator and scanners to create a raster-type pattern consisting of pixels containing signal information. Horizontal and vertical scanners are used to direct the photon stream, and optical elements are employed to project the scanning beam of light through the patient's pupil onto the retina to form an image. Either coherent or non-coherent light may be used. Images are created by the system's computer software, and full-color images are possible. For color images, red, green, and blue light sources are used, and the desired color is obtained by modulation and mixing of the three light sources. Instead of creating an image on a screen, the virtual retinal display projects the image directly onto the human retina, allowing the user to 'see' the image without viewing it on a secondary surface. Currently known applications for VRD technology are heads-up-displays, color projection systems for entertainment, or flight training simulators.

The present invention incorporates a virtual retinal display to create an environment of virtual reality, resulting in a visual function testing system of greatly increased capability. Virtual reality is a term applied loosely to the experience of an individual when exposed to the appearance of surroundings which are presented by interactive apparatus for stimulation of the senses. The primary cues are usually visual, supplemented by audio, and the feedback to the apparatus is generally by physical movements of the individual experiencing the virtual reality, such as pressing a button or a switch, or speaking into a microphone.

The virtual reality visual field measuring method and apparatus of the present invention uses a head-mounted apparatus for the presentation of visual and audio stimuli to a patient. The head-gear apparatus, configured as goggles, a facemask, or other suitable head-gear, which remains in a fixed spatial relationship to the patient's head during testing of the visual field, is adjustable to suit the individual patient, and is mounted on the patient's head by conventional means. A virtual retinal display is incorporated into the head-gear, so as to project through the pupil of the patient, via scanners, a light signal consisting of pixels, with color, if desired, so as to provide a full field of view for each eye. The virtual retinal display, in essence, "paints" the desired symbol, icon, dot of light, or other imagery, directly onto the patient's retina.

The visual image which is projected onto the retina of the patient by the virtual retinal display can have both relatively fixed image information, and superimposed visual stimuli, which may vary in time, place, size, shape, color, and intensity. These stimuli are generated and controlled by software in an associated computer, which receives interactive feedback from the patient. Such feedback includes, but is not limited to, direction of gaze sensing, eyelid movement and blinking, and audio and hand pressure signals as the patient responds to visual stimuli presentations.

The head-gear is provided with an integral microphone and speaker, for audio communication and feedback, and a multi-element gaze-aim sensor array. This ensemble is connected, by appropriate means, to a computer which provides the necessary visual and audio stimuli for the patient, and which receives the feedback responses to enable interactive functioning of the system. A hand-operated switch is incorporated.

Content of the software is dictated by the need to provide technically acceptable protocols. Such protocols provide for examining wide and narrow fields of view, selected areas, such as the blind spot or the fovea, and measurements of thresholds for sensitivity to light intensity, or, if desired, color, such as blue-on-yellow, or yellow-on-blue, or other color combinations. Measurements are usually made for one eye at a time, each looking at the same, or similar, fields of view.

Any desired imagery can be provided in the "background," or a conventional, uniform featureless field can be used. The background in various quadrants/areas may include patterns, or low-contrast images, and if present, these images may move quickly or slowly. Further, the intensity or color of the background may be changed, and any image, color, or brightness can be modulated over time. The shape, intensity, color, location, and duration of the superimposed test points also may be changed, and these characteristics can be modulated over time.

The foveal region of the retina contains a high density of cones, the color sensitive receptors, and the rest of the retina is populated mainly by rods, which are relatively insensitive to color. Therefore, the use of a test stimulus of a first color superimposed on a background of a second color is a beneficial practice to be incorporated in some visual field testing, especially in peripheral visual field testing. This practice is known to improve the sensitivity of visual field testing, resulting in earlier detection of glaucomatous damage. This advantage can be employed by using various combinations of colors. It has been determined that a particularly beneficial combination of colors is the use of a blue test stimulus on a yellow background.

In the present invention, a test stimulus of a first color, preferably blue, can be superimposed on a background of a second color, preferably yellow, either for viewing by both eyes, or for viewing by only one eye. The second eye can be presented with only a background of the second color. Presenting the color-on-color image for only one eye can be useful in preventing retinal rivalry, thereby reducing the stress imposed upon the patient during testing.

Whether viewed by one eye or both, if yellow is used for the background, it produces a relatively strong excitation of the medium wave length and long wave length retinal cone receptors, while producing little or no excitation of the short wave length retinal cone receptors. On the other hand, if blue is used for the test stimulus, it produces a relatively strong excitation of the short wave length retinal cone receptors, while producing little or no excitation of the medium wave length and long wave length retinal cone receptors.

Active feedback sensing alerts the system to patient loss of attention in general, or loss of fixation in particular, for notation and reiteration of test stimuli. In the presently described method and apparatus, provision is also made for reiteration of individual test points when a result is found to be inconsistent with a predetermined norm, or when lack of concentration or poor cooperation becomes evident, with appropriate care taken to provide no leading cues which may cause false positive or false negative responses. The software allows optional restful imagery to be provided in the "background," in addition to a conventional, uniform featureless field. The imagery in various quadrants or areas may be patterns, or low-contrast images, and may move quickly or slowly, and may have intensity, color, or temporal modulation. A hard-copy printout documenting patient responses is provided for the physician's records.

An element of this virtual retinal display testing system is that it allows the patient the freedom to shift his or her gaze, while in the test mode, without disruption of the process, thus relieving one of the causes of patient stress. Another feature provided is the ability to modulate the background scene brightness, contrast, color, optical stimulus size and detail, and duration of the test stimuli, all of which serve to relieve fatigue of the patient. Furthermore, the patient may move around bodily, since the head-gear is portable and, in addition, electrical interface to the computer may be wireless.

The occlusion of one eye while testing the fellow eye, required by conventional visual field testing, is eliminated in the preferred embodiment. Since both eyes can receive virtual retinal display images simultaneously, or separately and independently, provision is made to supply test stimuli to the specific eye being measured. The non-testing portion of the formed image can be generated separately for each eye by means of individual virtual retinal displays, or may be provided by a common VRD source and directed to both eyes simultaneously via a beam splitter.

One embodiment employs a single virtual retinal display apparatus and a beam splitter. In this system, non-varying background imagery is created equally in both eyes. By way of example, in one sequence of electronically-generated VRD images, odd images can correspond to the left eye, and even images can correspond to the right eye. During the test performance, in such a system, test stimuli would be non-simultaneously added to the odd images to test the left eye, or to the even images to test the right eye, thus eliminating the need to occlude either eye while the fellow eye is being tested.

In a dual-VRD embodiment, two virtual retinal displays are utilized, with one VRD projecting onto the retina of one eye, and the second VRD projecting onto the retina of the fellow eye. Appropriate software controls the testing in such a way that each eye receives test stimuli independently and non-simultaneously, eliminating the need for ocular occlusion. Thusly, the test stimuli are directed to the specific eye undergoing testing from a separate VRD source.

Because it is desirable to evaluate full, rather than partial, visual fields, the virtual retinal display system which is used for forming the wide angle virtual image has a demanding entrance angle requirement. This requirement can be met by trading image resolution for wider angle, for example, by reducing the numerical aperture. Such may be accomplished by using optical imaging elements, such as a Fresnel lens, or mirror, in which the large curvatures needed are obtained in a thin element, without the penalty of a bulky conventional lens. For the purpose of visual field testing, high resolution image formation is not a necessity, since the objective is to examine extramacular retinal regions and assess function thereof. For testing of macular function, such as visual acuity, the central region of a Fresnel lens can provide sufficient resolution to accomplish the task.

In appropriate tests, it may not be necessary to provide compensation for pupil displacement with respect to the optical axis of the image forming system, instead utilizing feedback from the pupil-motion sensing element (gaze tracker) to discard measurements when pupil displacement exceeds pre-set tolerances.

Figure 1:
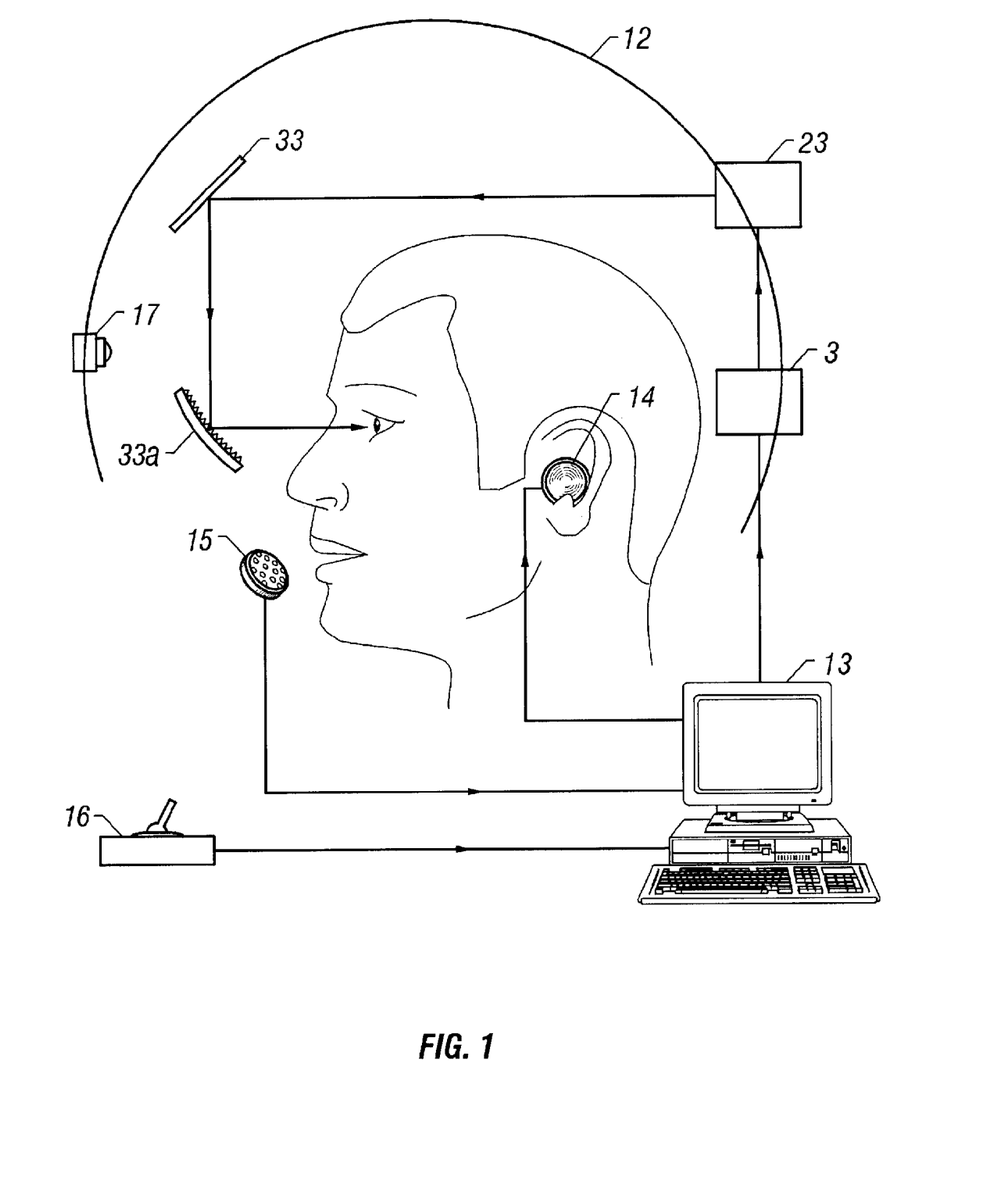
FIG. 1 is a schematic illustration of the apparatus of the present invention.
Figure 3A:
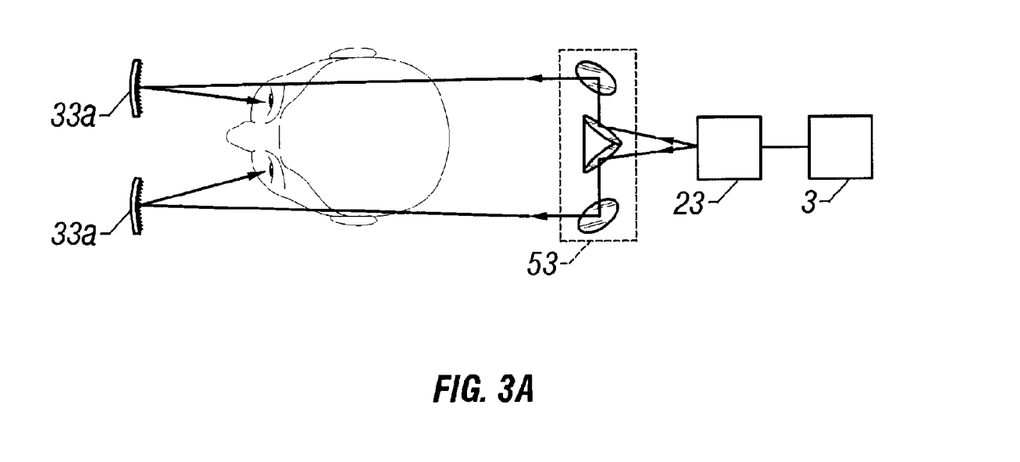
FIG. 3A is a schematic illustration of the apparatus shown in FIG. 1, with a beam splitter.

FIG. 1 shows the preferred embodiment, in which a head-mounted apparatus 12, such as goggles, facemask or other suitable head-gear, is connected to a computer 13. Software on the computer 13 is written to cause the computer 13 to generate a signal for the ultimate display of dots, symbols, or other imagery, through the pupillary aperture onto the patient's retinae. These computerized image signals are transmitted to the virtual retinal display 3, which generates the visual images. The visual images are transmitted via a system of deflection and directing optics 23, a redirection mirror 33, and then to a curved Fresnel redirection mirror 33a, and thence into the eye through the pupil. Other redirection apparatus types and configurations can also be used, some of which are described below. The system of deflection and directing optics 23 provides angular deflection of the image beam in vertical and horizontal axes to direct the photon beam to the desired location upon the retina. A beam splitter 53, as depicted in FIG. 3A, can be used to split the image beam into two separate beams for projection onto the two retinae. The computer 13 also generates and transmits an audio signal to a head-mounted earphone 14. A microphone 15 provides a feedback audio response from the patient to the computer 13. A hand-actuated switch 16 provides manual feedback from the patient to the computer 13. An optical sensor 17, mounted in the direction of gaze, provides gaze direction feedback to the computer 13.

Figure 2A:
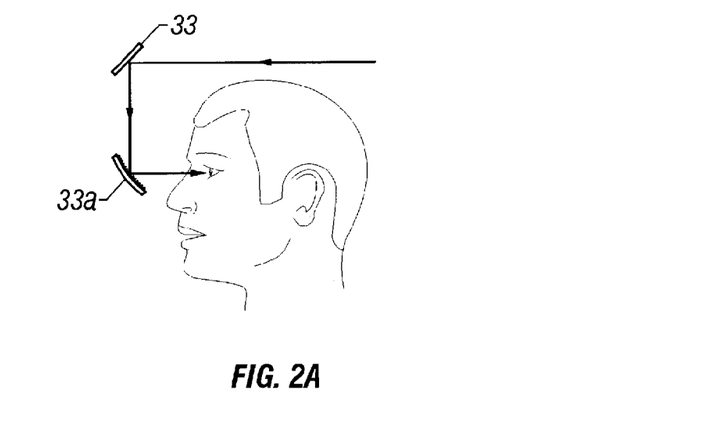
FIG. 2A is a schematic illustration of the apparatus shown in FIG. 1, with a curved Fresnel mirror redirection element.
Figure 2B:
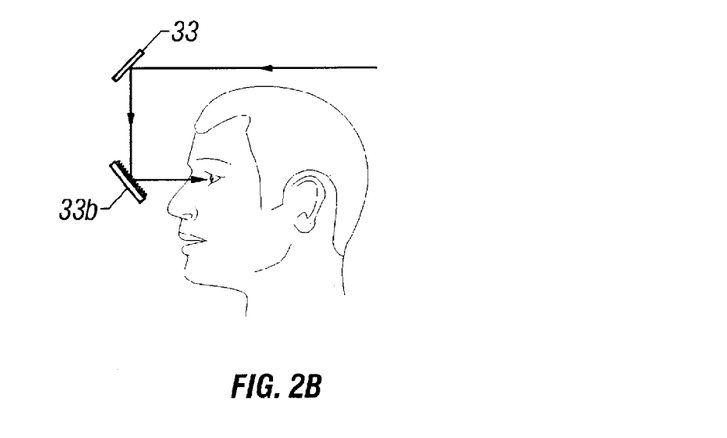
FIG. 2B is a schematic illustration of the apparatus shown in FIG. 1, with a flat Fresnel mirror redirection element.
Figure 2C:
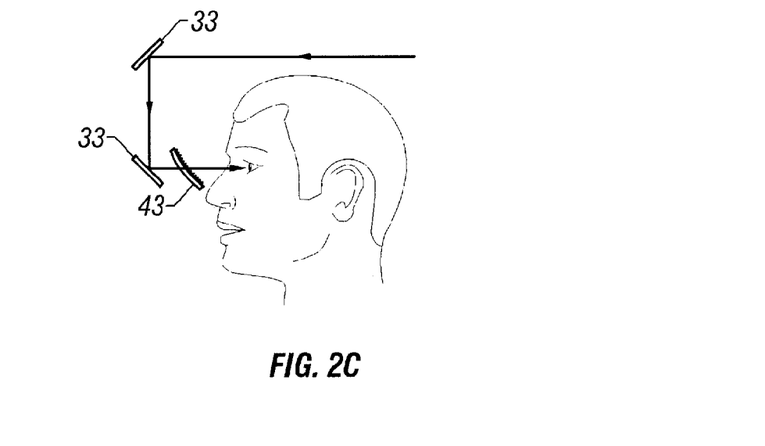
FIG. 2C is a schematic illustration of the apparatus shown in FIG. 1, with a dual mirror/Fresnel lens redirection element.

FIGS. 2A, 2B, and 2C depict alternate Fresnel optical element configurations for redirecting the image beam. The preferred embodiment is depicted in FIG. 2A, in which the final redirecting optical element is a curved Fresnel mirror 33a. An alternate embodiment is shown in FIG. 2B, in which a flat Fresnel mirror 33b, is incorporated. A further alternate embodiment is illustrated in FIG. 2C, showing dual redirecting mirrors 33, from which the stimulus passes through a curved Fresnel lens 43, en route to the eye. FIGS. 2A, 2B, and 2C, are intended to be merely a few examples of possible redirecting element configurations.

FIG. 3A depicts a schematic view of the preferred embodiment, shown from the top to illustrate the projection of separate beams into the two eyes of the patient. This embodiment utilizes a single virtual retinal display 3, and a single system of deflection and direction optics 23, with the image passing through a beam splitter 53, which splits the beam into two image beams for further transmission to both eyes. Under the control of the computer 13, the image beam can be projected onto only one eye at a time, if desired. Thusly, both eyes receive computer-directed, sequenced stimuli from a single virtual retinal display 3, and from a single system of deflection and directing optics 23. This is more economical, lighter, and much more patient-friendly.

Figure 3B:
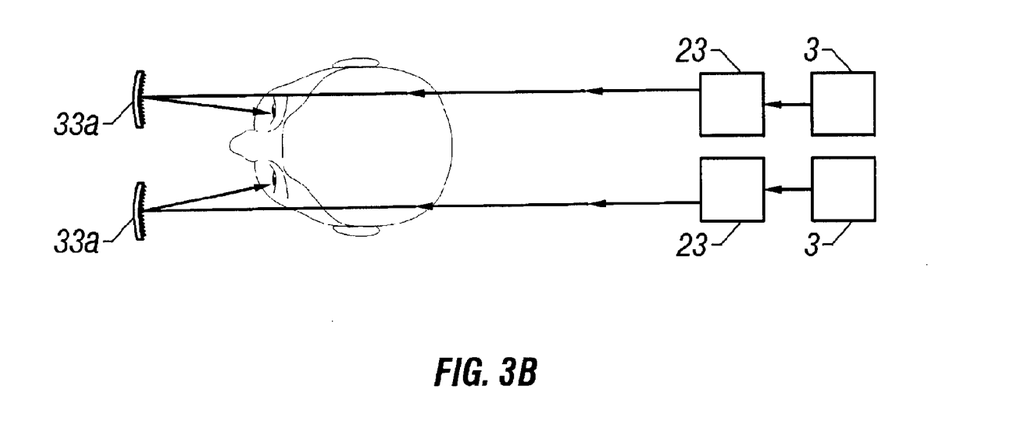
FIG. 3B is a schematic illustration of the apparatus shown in FIG. 1, with dual virtual retinal displays.

FIG. 3B shows an alternate embodiment incorporating dual virtual retinal displays 3, dual deflection and directing optics systems 23, and an absence of a beam splitter.

Figure 4A:
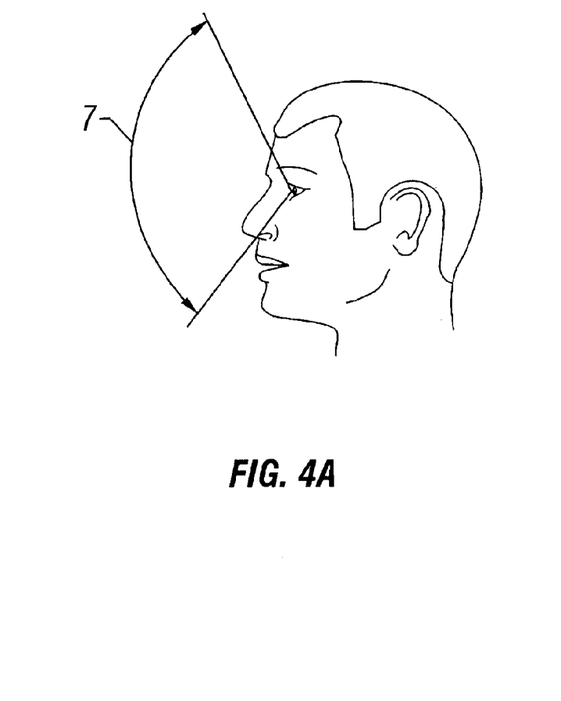
FIG. 4A is an illustration of the vertical field of view.
Figure 4B:
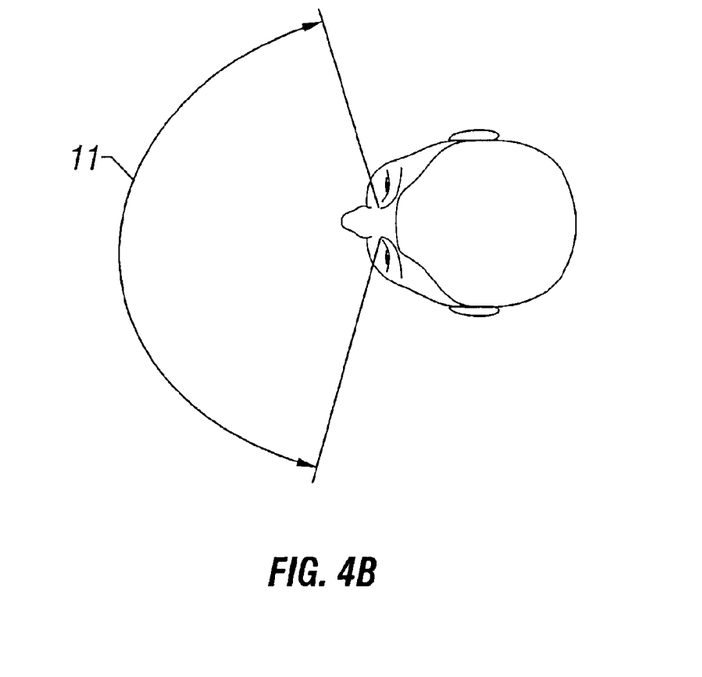
FIG. 4B is an illustration of the horizontal field of view.

FIG. 4A illustrates a vertical angular field of view 7, over which the image can be displayed. FIG. 4B shows a horizontal angular field of view 11, over which the image can be displayed.

Figure 5:
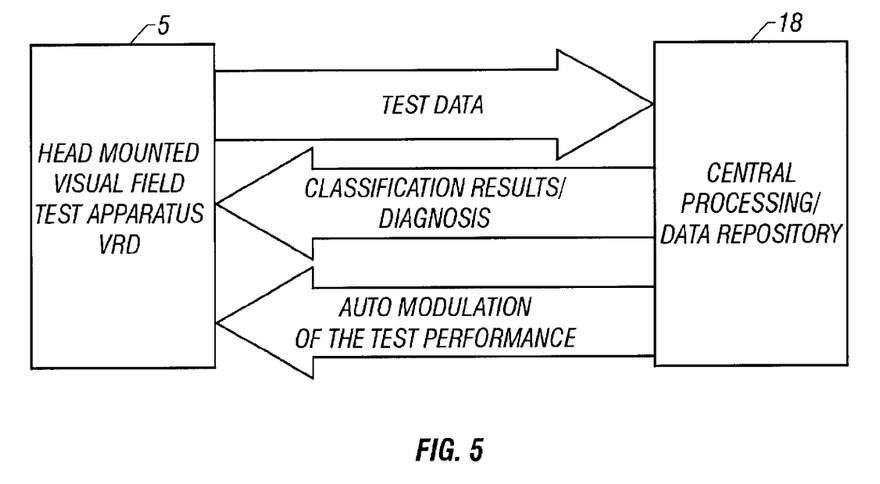
FIG. 5 is a schematic diagram of the information flow in the system of the present invention.

The system of the present invention, as illustrated in FIG. 5, includes a local visual field test apparatus 5, which can include a head mounted virtual retinal display apparatus 12, and a local processing system 13 which can form an integral part of the head-mounted diagnostic apparatus 12. The expert supervision of the testing process and interpretation of the results can be performed via long-distance transmission vehicles, such as the Internet, thus providing, telemetrically, not only essentially instantaneous autointerpretation, but also telemetric monitoring of the patient's performance of the test in real time. A central world-wide processing/data collection system 18 (consisting of a single station or a series of stations, such as one for the United States, one for Japan, one for France, etc.) can be linked via the Internet to a multitude of local test stations 5 and provide multiweb-like integration. The data processing portion of the system incorporates the local processing system 13 and the central processing system and data repository 18, to provide the classification of the visual field test data in terms of presence or absence of all diseases, or any particular disease (e.g., glaucoma). The data processing portion of the system also may assign a probability of detection and/or a numerical value indicating the severity of the disease. This provides a tool for monitoring disease progression.

Functions of the local processing system include the following:
  (a) provision of visual stimuli,
  (b) automatic customization of the stimuli sequence based on the patient response, including repetition of the stimuli for which no adequate response was registered (due either to the patient's loss of attention or to disease-induced damage to the visual field), and adjustment of the amplitude of stimuli, and
  (c) pre-processing of the patient response data, such as elimination of those measurement points (patient's responses) that are deemed inadequate, normalization to a pre-defined standard, and formatting for transmission to the remote processing system.

Functions of the remote processing system include the following:
(a) automatic interpretation of the visual field test data, and
(b) formulation of corrections to the data collection protocol, based on the results of auto-interpretation and comparative analysis employing the database of interpreted and medically verified visual field tests.

Figure 6:
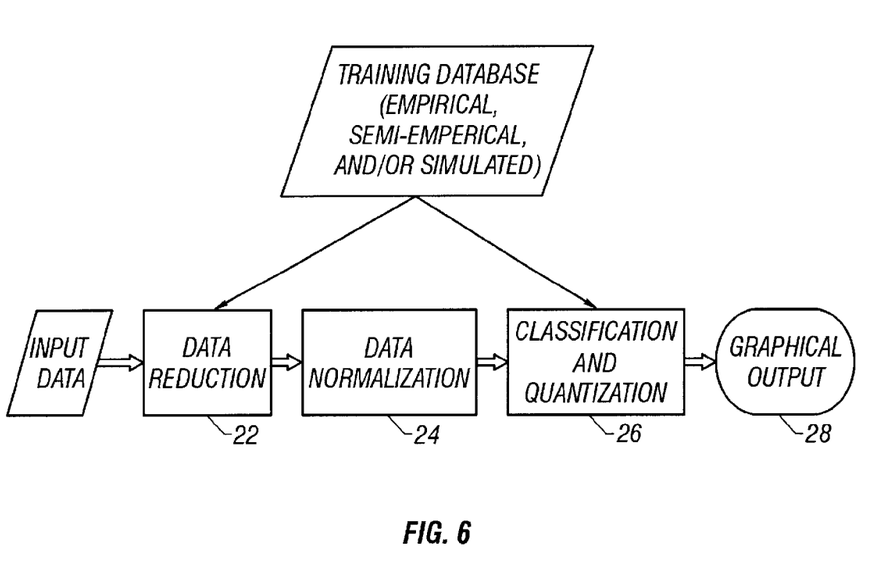
FIG. 6 is a schematic diagram of the automatic interpretation portion of the system of the present invention.

The central processing/data collection system 18 includes an automated interpretation system, incorporating a neural network, which functions as shown in FIG. 6. Integration of a multitude of local testing stations 5 into a world-wide system results in a telemedicine system which is "intelligent" in that ongoing data accumulation and analyses thereof improve the computational model and provide, over time, increasingly more accurate identification of very subtle disease processes.

A database of empirical, semi-empirical, or simulated visual field test data is used to build a neural network model of the visual field test data. This model, when applied to previously unseen test results, is capable of automatically interpreting and classifying the test data in terms of the presence and/or severity of abnormal (diseased) regions and states.

The auto-interpretation system utilizes the results of visual stimuli (consisting of dots, symbols, shapes, or patterns, with or without color, etc.) presented to the patient, which are converted into numerical representation for data processing, such as in the standard automated perimetry schemes (cf. Humphrey Field Analyzer). Other inputs, resulting from standard pre-processing of the test data, such as visual field indices, can also be employed by the neural network. Inclusion of all available individual components of perimetric examination is useful for proper clinical interpretation of the visual test examination. Thus, the information provided to the neural network may include:
(a) ancillary data, such as pupil size during testing, the patient's age, and visual acuity;
(b) reliability indices, such as fixation behavior and accuracy, and response fluctuation;
(c) visual field indices, such as average deviation of sensitivity at each test location from age-adjusted normal population values, the index of the degree of irregularity of visual field sensitivity about the normal slope, and sensitivity analysis of clusters of points;
(d) results of point-by-point comparison of test results with age-matched normal population values;
(e) results of high-pass resolution perimetry, if available from the given implementation of the test apparatus; and,
(f) results of pattern discrimination perimetry and other available tests.

The use of the entire gamut of available information for automatic interpretation by the neural network is also novel. Previously known neural network systems included only the straight visual field data.

The preferred embodiment of the neural network based auto-interpretation system is shown in FIG. 6. The system consists of some or all of the modules described below.

The data reduction module 22 is employed to reduce the size of the data vector presented to the neural network classifier. This module employs singular value decomposition, principal component analysis (PCA), learning vector quantization, or other clustering and data size reduction methods. Typically, application of any of these methods results in at least a two-fold decrease in the size of the data vector. Such a reduction increases the ability of the neural network to generalize the data contained in the training set. The clustering and linear decomposition methods (such as PCA) are also useful for 'novelty detection', i.e., for establishing if the current data vector is outside the region encompassed by the training data set. The neural network model is likely to fail for such data and thus, the ability to detect novelty is crucial for minimizing the number of erroneous interpretations.

The data normalization module 24 performs amplitude normalization of the data presented to the neural network.

The neural network classifier module 26 performs pattern recognition and classification of the visual field test data. The probability of classification (or, degree of membership) is quantified for each of the classes considered in the model. In the preferred embodiment, a non-linear classification scheme exemplified by the multilayer perceptron or the radial/ellipsoidal basis function neural network is used. However, other classification schemes such as multivariate analysis, linear regression, statistical classifiers or discriminators (such as Bayesian classifiers) may also be employed. The neural networks are especially useful for the automatic application scheme because they provide a non-parametric, empirical model of the visual field test data and are computationally non-intensive, i.e., the classification computations can be performed quickly on inexpensive computers.

The neural network may be a binary classification system, which will indicate the presence or absence of a particular disease, such as glaucoma, or a multi-class system, which provides recognition and classification of a large variety of possible visual field disorders, including, but not limited to, neurological tumors, cerebrovascular accidents and strokes, optic nerve disorders, compression syndromes of the optic nerve or optic chiasm, demyelinating diseases, and diseases of the retina.

The implementation may be in the form of a single-level neural network system or a hierarchical system. In the single-level system, all the input data, which are deemed relevant for the interpretation task, are inputted and processed simultaneously. In the hierarchical system, different input data types are modeled by dedicated separate subsystems, and these outputs are subsequently fused through a suitable computational architecture, to produce the final classification result.

The output module 28 creates a graphical representation of the visual field test data, such as isopter/scotoma plots, or gray scale or color-coded plots, with superimposed identification of the regions that the system classified as abnormal.

The automatic interpretation system is an expert system trained on a set of empirical, semi-empirical, and/or simulated data. The construction of a proper training database is essential for achieving good performance of the interpretation system (good sensitivity and specificity). The training database may contain all, or any, of the following types of visual field data:
(a) empirical data, i.e., data obtained for patients with normal and abnormal visual fields;
(b) semi-empirical data, i.e., data obtained by modification of the empirical data, as described above, by:
(1) emphasizing or de-emphasizing certain aspects of the visual field test to bring out the characteristic features of certain diseased states;
(2) adding noise or measurement uncertainty components which may be associated with a real visual field examination; and, (3) any other modification of the visual field test data and their associated classification; and, (c) simulated data, i.e., data that are constructed to simulate the real-world results of a visual field test for both normal and abnormal visual fields.

Training of the classification system is performed off-line with active participation of a human expert. That is, all visual field test data in the training database are examined by an expert and the medical diagnosis is verified and validated before the data is used to build the neural network model. The centralized processing enables collection of a large number of diverse examples of normal and abnormal visual field test data. The novelty detection capability of the system alerts the system custodian to the necessity for expert examination of the novel data. After completion of such examination, the data may be included in the model by including the new data in the training database and re-training the system.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual function testing apparatus, comprising:
    a light source, said light source being modulated to create an image;
    a scanning system, said scanning system being adapted to scan said image from said light source onto a retina of an eye of a patient;
    a gaze sensing device adapted to sense the orientation of an eye of a patient and to generate a gaze orientation signal;
    a response sensing device adapted to sense a patient's response to said image and to generate a response signal; and
    a computer, said computer being connected to said light source to modulate said light source to create said image, said computer being connected to said gaze sensing device to receive said gaze orientation signal, said computer being connected to said response sensing device to receive said response signal, and said computer being programmed to interpret said gaze orientation signal and said response signal to evaluate at least one visual function of the patient.

2. A visual function testing apparatus as recited in claim 1, wherein said scanning device is mountable to the head of a patient.

3. A visual function testing apparatus as recited in claim 1, wherein said computer is programmed to vary at least one characteristic of said image.

4. A visual function testing apparatus as recited in claim 1, wherein said response sensing device comprises a switch manipulated by the patient.

5. A visual function testing apparatus as recited in claim 1, wherein said response sensing device comprises a motion detector.

6. A visual function testing apparatus as recited in claim 1, wherein said response sensing device comprises a sound detector.

7. A visual function testing apparatus as recited in claim 1, wherein said response sensing device comprises a gaze sensor.

8. A visual function testing apparatus as recited in claim 1, further comprising an optical system for directing said image from said scanning system onto the retina of an eye of a patient.

9. A visual function testing apparatus as recited in claim 1, further comprising a redirection element for redirecting said image onto the retina of an eye of a patient.

10. A visual function testing apparatus as recited in claim 9, wherein said redirection element comprises a Fresnel optical element.

11. A visual function testing apparatus as recited in claim 10, wherein said Fresnel optical element comprises a Fresnel mirror.

12. A visual function testing apparatus as recited in claim 10, wherein said Fresnel optical element comprises a Fresnel lens.

13. A visual function testing apparatus as recited in claim 1, further comprising a beam splitter adapted to split said image from said light source to create a separate image for scanning onto each eye of a patient.

14. A visual function testing apparatus as recited in claim 1, where said computer is programmed to analyze said signals to recognize faulty data on said visual function of the patient.

15. A visual function testing apparatus as recited in claim 1, wherein said computer is programmed to shift said image to a desired location relative to said gaze orientation of the patient.

16. A visual function testing apparatus, comprising:
    a light source, said light source being modulated to create an image;
    a scanning system mountable to the head of a patient, said scanning system being adapted to scan said image from said light source onto a retina of an eye of a patient;
    a beam splitter adapted to split said image from said light source to create a separate image for scanning onto each eye of a patient;
    two redirection elements for redirecting said separate images onto the retinae of the eyes of a patient;
    a gaze sensing device adapted to sense the orientation of each eye of a patient and to generate a gaze orientation signal;
    a response sensing device adapted to sense a patient's response to said images and to generate a response signal; and
    a computer, said computer being connected to said light source to modulate said light source to create said image, said computer being connected to said gaze sensing device to receive said gaze orientation signal, said computer being connected to said response sensing device to receive said response signal, and said computer being programmed to interpret said gaze orientation signal and said response signal to evaluate at least one visual function of the patient.

17. A method for analyzing at least one visual function of a patient, said method comprising:
    providing a light source connected to a computer;
    mounting a display device to the head of a patient, said display device including an image scanning system and a gaze sensing device, said display device being connected to said computer;
    modulating said light source with said computer to generate an image;
    scanning said image from said light source onto a retina of an eye of the patient, with said scanning system;
    sensing the orientation of the eye of the patient and generating a gaze orientation signal;
    sensing the patient's response to said image and generating a response signal; and interpreting said gaze orientation signal and said response signal with said computer to evaluate at least one visual function of the patient.

18. A method as recited in claim 17, further comprising splitting said image from said light source with a beam splitter, to create a separate image for scanning onto each eye of the patient.

19. A method as recited in claim 17, further comprising analyzing said signals with said computer to recognize faulty data on said visual function of the patient.

20. A method as recited in claim 17, further comprising shifting said image to a desired location relative to said gaze orientation of the patient.

21. A multiple site visual field testing system, comprising:
    a plurality of virtual retinal display devices, each said display device being constructed and positioned to project an image onto the retina of at least one eye of the respective patient;
    a plurality of response sensing devices, each said response sensing device being adapted to sense a respective patient's response to a visual stimulus and to generate a response signal;
    a plurality of local signal processing systems, each said local processing system being connected to a respective said display device to generate said image, each said local processing system being connected to a respective said response sensing device to receive said response signal;
    a central processing system connectable to said plurality of local signal processing systems for controlling generation of said images, and for receipt of said response signals from said plurality of local processing systems;
    a neural network for automatic interpretation of said response signals; and
    a central data repository for collection of data from said response signals, and for repetitive training of said neural network.

22. A visual field testing system as recited in claim 21, wherein each said virtual retinal display device is mounted in a substantially motionless relationship to the head of a patient, while allowing the head to move.

23. A visual field testing apparatus as recited in claim 21, wherein said central processing system is connectable to said plurality of local signal processing systems via the Internet.

24. A method for automatically analyzing the visual fields of a plurality of patients, comprising:
    providing a virtual retinal display device, a response sensing device, and a local signal processing device for each of a plurality of patients;
    displaying an image on at least one retina of each patient;
    sensing each patient's response to said image and generating a response signal for each patient;
    controlling generation of each said image and receiving each said response signal with a central processing system; and
    analyzing at least one characteristic of the visual field of each patient with a central neural network.

25. A method as recited in claim 24, further comprising connecting said central processing system to each said virtual retinal display device, response sensing device, and local signal processing device via the Internet, for controlling the generation of each said image and receiving each said response signal.

26. A visual field testing apparatus, comprising:
    a light source, said light source being modulated to create an image;
    a scanning system, said scanning system being adapted to scan said image from said light source onto a retina of an eye of a patient, said image being enhanced by color selection;
    a gaze sensing device adapted to sense the orientation of an eye of a patient and to generate a gaze orientation signal;
    a response sensing device adapted to sense a patient's response to said image and to generate a response signal; and
    a computer, said computer being connected to said light source to modulate said light source to create said image, said computer being connected to said gaze sensing device to receive said gaze orientation signal, said computer being connected to said response sensing device to receive said response signal, and said computer being programmed to interpret said gaze orientation signal and said response signal to evaluate at least one visual function of the patient.

27. A visual field testing apparatus as recited in claim 26, wherein:
    said image further includes a background upon which a test stimulus is displayed;
    said test stimulus exhibits a first color; and
    said background exhibits a second color different from said first color.

28. A visual field testing apparatus as recited in claim 27, wherein said first color is blue and said second color is yellow.

29. A method for measuring at least one characteristic of the visual field of a patient, comprising:
    mounting a virtual retinal display apparatus in a substantially motionless relationship to the head of a patient, while allowing the head to move, said virtual retinal display apparatus including at least one sensing device, said virtual retinal display apparatus being connected to a computer;
    displaying an image generated by said computer, said image being projected onto the retina of at least one eye of the patient, said image including a test stimulus;
    enhancing the visibility of said test stimulus by color selection;
    sensing the orientation of at least one eye of the patient and generating a gaze orientation signal;
    sensing the patient's response to said image and generating a response signal;
    receiving said gaze orientation signal and said response signal with said computer and calculating at least one characteristic of the visual field of the patient.

30. A method as recited in claim 29, further comprising:
    displaying said test stimulus on a background; and
    enhancing said visibility of said test stimulus by displaying said test stimulus in a first color and displaying said background in a second color different from said first color.

31. A method as recited in claim 30, further comprising:
    displaying said test stimulus in blue; and
    displaying said background in yellow.

* * * * *